United States Patent [19]

Inoue et al.

[11] Patent Number: 4,788,311
[45] Date of Patent: Nov. 29, 1988

[54] NOVEL ORGANOSILICON COMPOUNDS USEFUL AS A STABILIZER FOR ORGANOPOLYSILOXANE COMPOSITIONS

[75] Inventors: Yoshio Inoue, Annaka; Takeo Inoue, Yokohama, both of Japan

[73] Assignee: Shin-Etsu Chemical Co., Ltd., Tokyo, Japan

[21] Appl. No.: 152,416

[22] Filed: Feb. 4, 1988

[30] Foreign Application Priority Data

Feb. 5, 1987 [JP] Japan .................. 62-25225

[51] Int. Cl.$^4$ .............................. C07F 7/08
[52] U.S. Cl. ................................ 556/435
[58] Field of Search ....................... 556/435

[56] References Cited

U.S. PATENT DOCUMENTS 3,666,783 5/1972 LeFort ............................ 556/435 X
3,793,358 2/1976 Bauer et al. ..................... 556/435 X

FOREIGN PATENT DOCUMENTS 60-81187 5/1985 Japan .................. 556/435

*Primary Examiner*—Paul F. Shaver
*Attorney, Agent, or Firm*—Lowe, Price, LeBlanc, Becker & Shur

[57] ABSTRACT

Novel organosilicon compounds of the following general formula

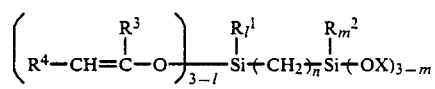

in which $R^1$ and $R^2$ independently represent an unsubstituted or substituted monovalent hydrocarbon group having from 1 to 8 carbon atoms, $R^3$ and $R^4$ independently represent a hydrogen atom or have the same meaning as $R^1$ and $R^2$, X has the same meaning as $R^1$ or is a group of the following formula

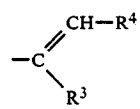

in which $R^3$ and $R^4$ have, respectively, the same meanings as defined above, l and m are, respectively, 0, 1 or 2, and n is an integer of from 2 to 8.

6 Claims, 3 Drawing Sheets

NOVEL ORGANOSILICON COMPOUNDS USEFUL AS A STABILIZER FOR ORGANOPOLYSILOXANE COMPOSITIONS

BACKGROUND OF THE INVENTION

Field of the Invention

This invention relates to hitherto unknown, novel organosilicon compounds which are useful as a stabilizer for room temperature vulcanizable organopolysiloxane compositions.

SUMMARY OF THE INVENTION

It is an object of the invention to provide new and hitherto unknown organosilicon compounds which are very useful as a stabilizer for room temperature vulcanizable organopolysiloxane compositions.

The above object can be achieved, according to the invention, by an organosilicon compound of the following general formula (I)

$$\left(R^4-CH=C-O\right)_{3-l}\overset{R_l^1}{\underset{|}{Si}}(CH_2)_n\overset{R_m^2}{\underset{|}{Si}}(OX)_{3-m} \quad (I)$$

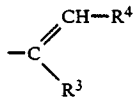

in which $R^1$ and $R^2$ independently represent an unsubstituted or substituted monovalent hydrocarbon group having from 1 to 8 carbon atoms, $R^3$ and $R^4$ independently represent a hydrogen atom or an unsubstituted or substituted monovalent hydrocarbon group having from 1 to 8 carbon atoms, X has the same meaning as $R^1$ or is a group of the following formula

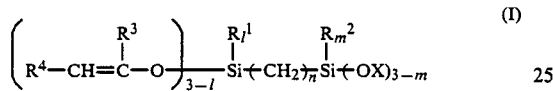

in which $R^3$ and $R^4$ have, respectively, the same meanings as defined above, l and m are, respectively, 0, 1 or 2, and n is an integer of from 2 to 8.

DETAILED DESCRIPTION AND EMBODIMENTS OF THE INVENTION

Figure 1:
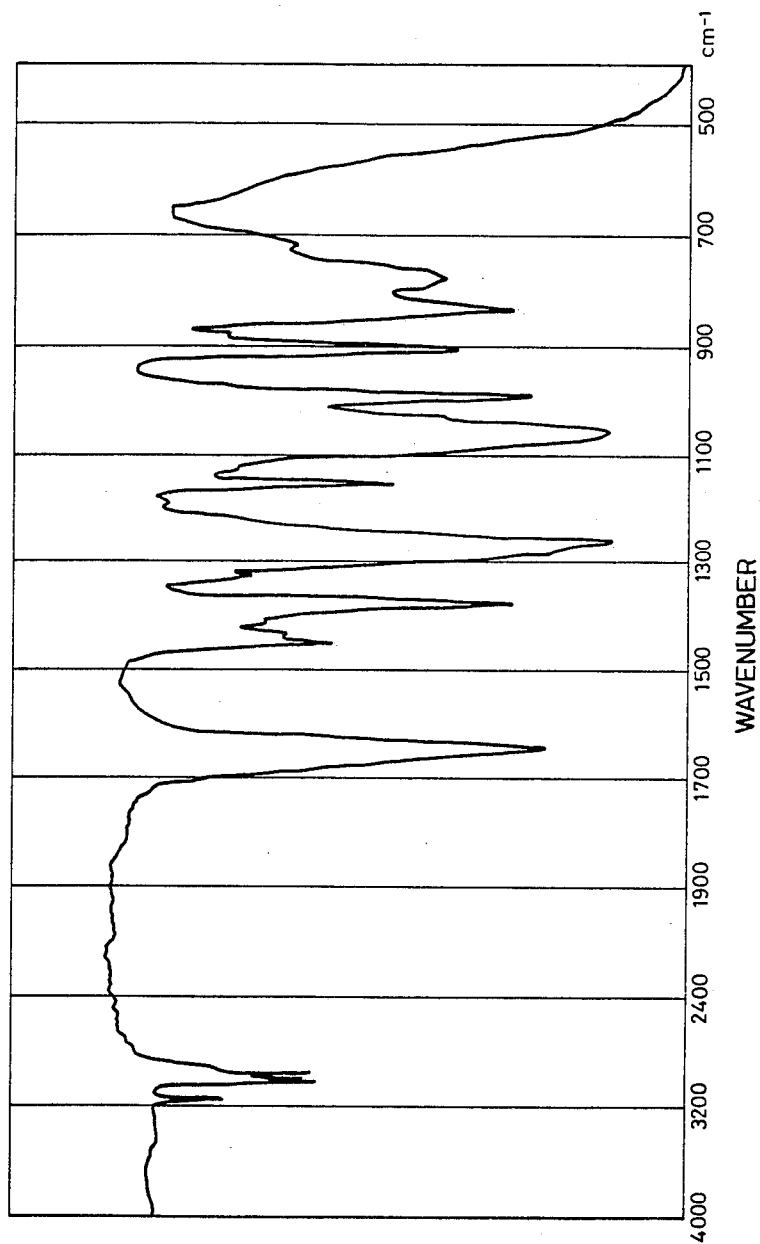
FIGS. 1 to 3 are infrared absorption spectrum charts of the organosilicon compounds obtained in Examples 1 to 3, respectively.

The organosilicon compounds according to the invention are represented by the formula (I) indicated above. In the formula, $R^1$ and $R^2$ are independently an unsubstituted or substituted monovalent hydrocarbon group having from 1 to 8 carbon atoms. The monovalent hydrocarbon groups include an alkyl group such as a methyl group, an ethyl group, a propyl group, a butyl group and the like, a cycloalkyl group such as a cyclohexyl group, an alkenyl group such as a vinyl group, an allyl group and the like, an aryl group such as a phenyl group, a tolyl group and the like, and part or all of the hydrogen atoms bonded to the above carbon atom or atoms substituted with a halogen atom such as a chlorine atom, an iodine atom, a bromine atom or a fluorine atom, or a cyano group, e.g. a chloromethyl group, a trifluoropropyl group, a cyanoethyl group and the like. $R^3$ and $R^4$ independently represent a hydrogen atom or have the same meanings as defined with respect to $R^1$ or $R^2$. X represents have the same meanings as $R^1$ or a group of the formula

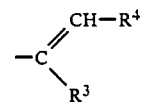

in which $R^3$ and $R^4$ have, respectively, the same meanings as defined above. Moreover, l and m are, respectively, a value of 0, 1 or 2, and n is an integer of from 2 to 8.

Preferably, $R^1$, $R^2$ and $R^3$ are independently an alkyl group, $R^4$ is a hydrogen atom, X is an alkyl group or a —C(CH$_3$)=CH$_2$ group, l is 0 or 1 and m is 0 or 1. Most preferably, $R^1$, $R^2$ and $R^3$ are independently a methyl group. Typical examples of the organosilicon compounds according to the invention are those compounds of the following formulae

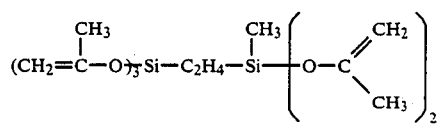

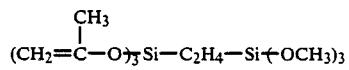

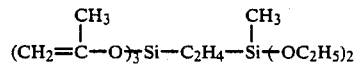

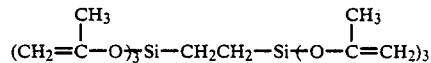

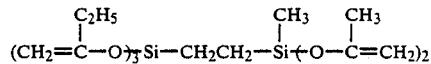

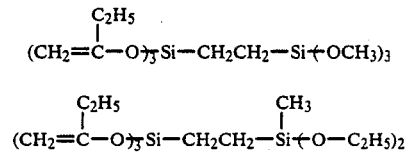

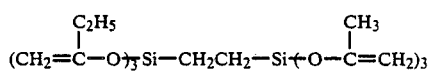

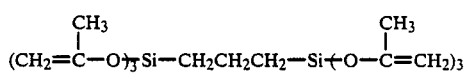

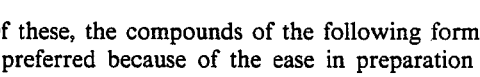

Of these, the compounds of the following formulae are preferred because of the ease in preparation and good economy

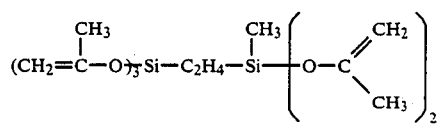

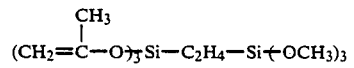

-continued

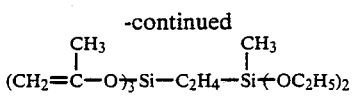

The organosilicon compounds of the formula (I) are prepared by reaction between an organosilicon compound of the following formula (II) blocked with a vinyl group at ends thereof

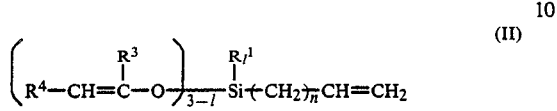

in which $R^1$, $R^3$, $R^4$, $l$ and $n$ have, respectively, the same meanings as defined before, and an organosilicon compound of the following formula (III)

in which $R^2$, X and m have, respectively, the same meanings as defined before. This reaction is an addition reaction which proceeds in the presence of a catalyst of a metal of the group VIII of the Periodic Table or its compounds such as, for example, platinum black, chloroplatinic acid, alcohol-modified chloroplatinic acid, platinum-vinylsiloxane, complexes of chloroplatinic acid and olefins or aldehydes, and the like. The amount of the catalyst is generally in the range of from 5 to 50 ppm, calculated as a metal, of the reaction mixture. The reaction may be effected in an aromatic hydrocarbon such as benzene, toluene, xylene or the like. The reaction conditions include a temperature of from 10° to 150° C. and a time of from 1 to 10 hours.

The starting organosilicon compound of the formula (II) is prepared by reaction between vinyltrichlorosilane and acetone, and the preparation of this compound (II) is described, for example, in Japanese Laid-open Patent Application No. 55-19201.

The organosilicon compound of the formula (I) according to the invention is particularly useful as a stabilizer of room temperature vulcanizable organopolysiloxane compositions of the type in which an organopolysiloxane blocked with a hydroxyl group at both ends thereof and an alkylsilicate or its hydrolyzate used as a crosslinking agent are reacted in the presence of a salt of a metal and an organic acid for dealcoholization.

The present invention is described in more detail in the following examples.

EXAMPLE 1

22.6 g (0.1 mole) of vinyltris(isopropenyloxy)silane, 0.81 g of an isopropyl alcohol solution of chloroplatinic acid (having a platinum content of 1.0 wt%) and 50 g of toluene were charged into a reactor and heated to a temperature of from 24° to 65° C. Thereafter, 15.8 g (0.1 mole) of methyldi(isopropenoxy)silane was dropped into the mixture in about 2 hours, whereupon the exothermic reaction proceeded and was accomplished at the time of completion of the dropping. The reaction solution was subjected to distillation under reduced pressure to obtain 36.2 g of a liquid product having a boiling point of 146° C./5 mmHg.

This product was subjected to measurement of physical properties, elementary analysis, measurement of a molecular weight by gas mass spectrometry, and IR absorption spectrum analysis. The results are summarized below, from which the product was confirmed to have the following formula

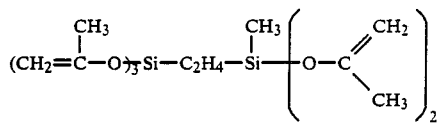

Specific gravity (25° C.): 0.9792.
Refractive index ($n^{25}$): 1.4500.
Molecular weight: 384.

| Elementary analysis | C | H | Si |
|---|---|---|---|
| Calculated for $C_{18}H_{32}Si_2O_5$ (%) | 56.25 | 8.33 | 14.58 |
| Found (%) | 55.30 | 8.29 | 14.49 |

IR absorption spectrum: see FIG. 1.

EXAMPLE 2

The general procedure of Example 1 was repeated except that 12.2 g (0.1 mole) of trimethoxysilane was used instead of the methyldi(isopropenoxy)silane, thereby obtaining 30.5 g of a liquid product having a boiling point of 141° C./8 mmHg. This product was similarly subjected to measurement of physical properties, elementary analysis, gas spectrometry, and IR absorption spectrum analysis with the following results, from which the product was confirmed to be of the following formula

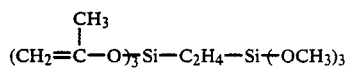

Specific gravity (25° C.): 1.0202.
Refractive index ($n^{25}$): 1.4340.
Molecular weight: 348.

| Elementary analysis | C | H | Si |
|---|---|---|---|
| Calculated for $C_{14}H_{28}Si_2O_6$ (%) | 48.27 | 8.05 | 16.09 |
| Found (%) | 48.16 | 8.10 | 16.04 |

Figure 2:
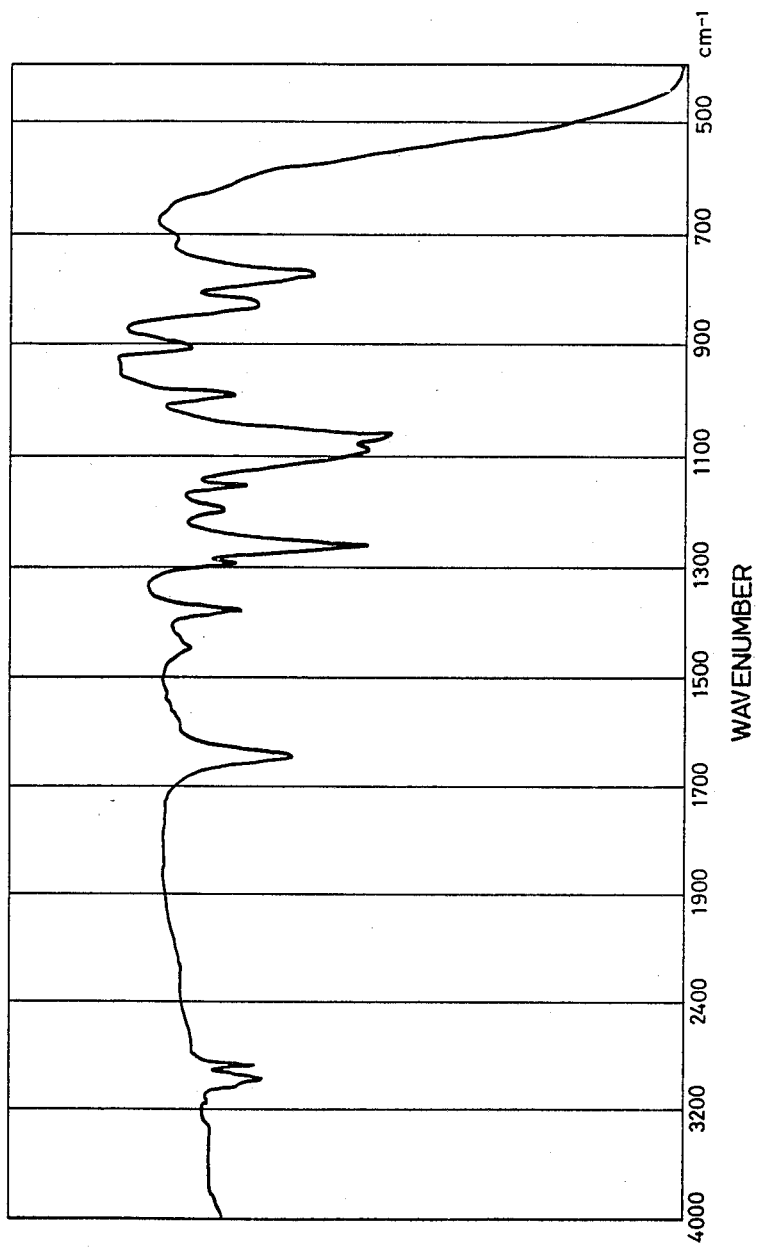

IR absorption spectrum: see FIG. 2.

EXAMPLE 3

The general procedure of Example 1 was repeated except that 13.4 g (0.1 mole) of methyldi(ethoxysilane) was used instead of the methyldi(isopropenoxy)silane, thereby obtaining 32.3 g of a liquid product having a boiling point of 147° C./11 mmHg. This product was subjected to measurement of physical properties, elementary analysis, gas mass spectrometry, and IR absorption spectrum analysis with the following results, from which the product was confirmed to be of the following formula

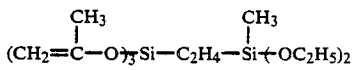

Specific gravity (25° C.): 0.9639.
Refractive index ($n^{25}$): 1.4400.
Molecular weight: 360.

| Elementary analysis | C | H | Si |
|---|---|---|---|
| Calculated for $C_{16}H_{32}Si_2O_5$ (%) | 53.33 | 8.89 | 15.55 |
| Found (%) | 53.01 | 8.90 | 15.24 |

Figure 3:
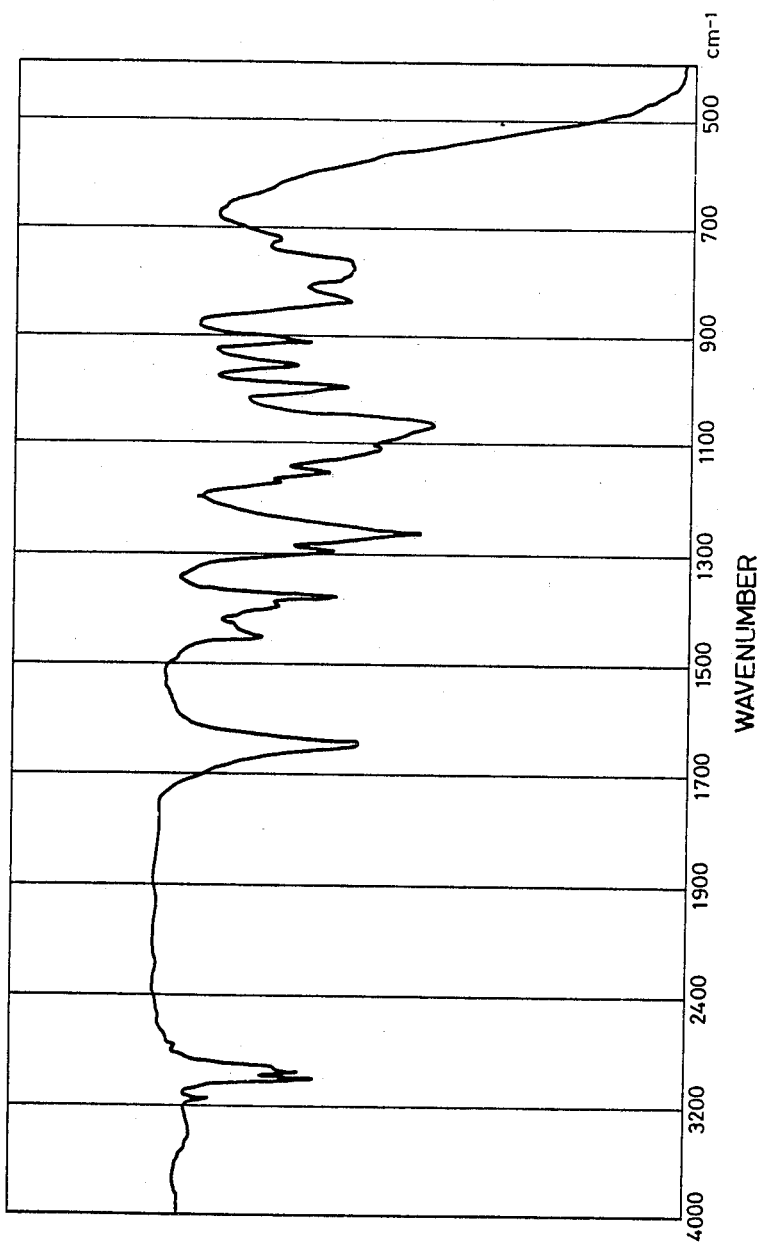

IR absorption spectrum: see FIG. 3.

What is claimed is:

1. An organosilicon compound of the following general formula (I)

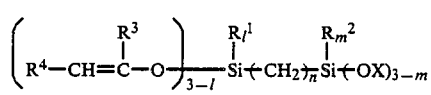

in which $R^1$ and $R^2$ independently represent an unsubstituted or substituted monovalent hydrocarbon group having from 1 to 8 carbon atoms, $R^3$ and $R^4$ independently represent a hydrogen atom or an unsubstituted or substituted monovalent hydrocarbon group having from 1 to 8 carbon atoms, X has the same meaning as $R^1$ or is a group of the following formula

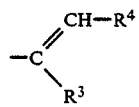

in which $R^3$ and $R^4$ have, respectively, the same meanings as defined above, l and m are, respectively, 0, 1 or 2, and n is an integer of from 2 to 8.

2. An organosilicon compound according to claim 1, wherein $R^2$ and $R^3$ are independently an alkyl group, $R^4$ is a hydrogen atom, X is an alkyl group or a $-C(CH_3)=CH_2$ group, l is 0 or 1 and m is 0 or 1.

3. An organosilicon compound according to claim 2, wherein $R^1$, $R^2$ and $R^3$ are independently a methyl group.

4. An organosilicon compound of the following formula

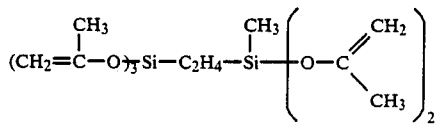

5. An organosilicon compound of the following formula

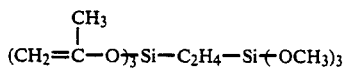

6. An organosilicon compound of the following formula

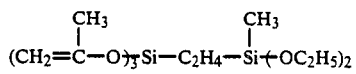

* * * * *